United States Patent
Adam et al.

[11] Patent Number: 6,166,209
[45] Date of Patent: Dec. 26, 2000

[54] PIPERIDINE DERIVATIVES

[75] Inventors: Geo Adam, Schopfheim, Germany; Andrea Cesura, Basel, Switzerland; Guido Galley, Rheinfelden, Germany; François Jenck, Riedisheim, France; Stephan Röver, Inzlingen; Jürgen Wichmann, Steinen, both of Germany

[73] Assignee: Hoffmann-La Roche Inc., Nutley, N.J.

[21] Appl. No.: 09/196,992

[22] Filed: Nov. 20, 1998

[30] Foreign Application Priority Data

Dec. 11, 1997 [EP] European Pat. Off. .............. 97121844

[51] Int. Cl.⁷ ...................... A61K 31/438; A61K 31/40; C07D 405/04

[52] U.S. Cl. ........................... 546/17; 514/278; 514/412; 514/413; 548/409; 548/410

[58] Field of Search .................................................. 546/17

[56] References Cited

U.S. PATENT DOCUMENTS 3,985,889  10/1976  Bauer et al. ............................ 514/278

FOREIGN PATENT DOCUMENTS

| | | |
|---|---|---|
| 2458176 | 6/1975 | Denmark . |
| 0 518 805 | 12/1992 | European Pat. Off. . |
| 0 856 514 | 8/1998 | European Pat. Off. . |

OTHER PUBLICATIONS

J. Org. Chem. vol. 41, No. 15, (1976) 2628–2633.

*Primary Examiner*—Alan L. Rotman
*Attorney, Agent, or Firm*—George W. Johnston; Patricia S. Rocha-Tramaloni; Robert A. Silverman

[57] ABSTRACT

The present invention relates to compounds of the formula

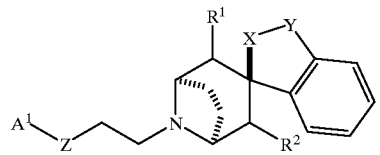

I-1 wherein
X is —O— or —CH₂—;
Y is —C(O)—, —(CH₂)$_n$— or —N(CH₃)—;
n is 1 or 2 or
X and Y taken together are —CH=CH—
Z is —NH—, —CH₂—, —O— or =CH—;
A¹ is a group

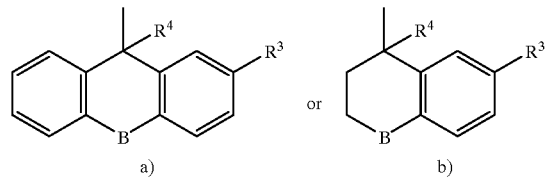

B is —(CH₂)$_m$—;
m is 0, 1 or 2;
R¹ and R² are each independently hydrogen or lower alkyl;
R³ is hydrogen or halogen;
R⁴ is hydrogen or hydroxy and
the dotted line is (—CH₂—CH₂—)$_{n'}$, and n' is 0 or 1 and to pharmaceutically acceptable acid addition salts thereof.

The compounds of the present invention are antagonists of the OFQ receptor. Consequently they will be useful in the treatment of memory and attention deficits, psychiatric, neurological and physiological disorders, especially, but not limited to, amelioration of symptoms of anxiety and stress disorders, depression, memory loss due to Alzheimer's disease or other dementias, epilepsy and convulsions, acute and/or chronic pain conditions, symptoms of addictive drug withdrawal, control of water balance, Na⁺ excretion and arterial blood pressure disorders and metabolic disorders such as obesity.

14 Claims, No Drawings

PIPERIDINE DERIVATIVES

BACKGROUND

Orphanin FQ (OFQ), a seventeen amino-acid-long peptide (F-G-G-F-T-G-A-R-K-S-A-R-K-L-A-N-Q), has been isolated from rat brain and is a natural ligand for a G-protein coupled receptor (OFQ-R), found at high levels in brain tissue.

OFQ exhibits agonistic activity at the OFQ-R both in vitro and in vivo.

Julius (Nature 377,476, [1995]) discusses the discovery of OFQ noting that this peptide shares greatest sequence similarity with dynorphin A, an established endogenous ligand for opioid receptors. OFQ inhibits adenylate cyclase in CHO(LC 132$^+$) cells in culture and induces hyperalgesia when administered intra-cerebroventricularly to mice. The pattern of results indicate that this heptadecapeptide is an endogenous agonist of the LC 132 receptor and it appears to have pro-nociceptive properties. It has been described that when injected intra-cerebroventricularly in mice, OFQ slows down locomotive activity and induces hyperalgesia and it has been concluded that OFQ may act as a brain neurotransmitter to modulate nociceptive and locomotive behavior.

An object of the invention is to provide compounds that are antagonists of the OFQ receptor. Antagonists of the OFQ receptor are useful for treating anxiety and stress disorders, depression, memory loss due to Alzheimer's disease or other dementias, epilepsy and convulsions, acute and/or chronic pain conditions, symptoms of addictive drug withdrawal, control of water balance, Na$^+$ excretion and arterial blood pressure disorders and metabolic disorders such as obesity.

SUMMARY OF THE INVENTION

The invention relates to a compound of the formula

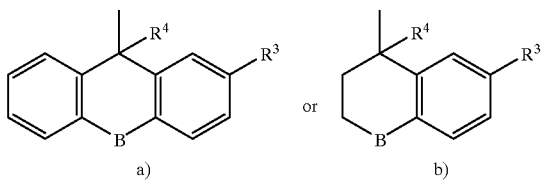

I-1 wherein

X is —O— or —CH$_2$—;
Y is —C(O)—, —(CH$_2$)$_n$— or —N(CH$_3$)—;
n is 1 or 2 or
X and Y taken together are —CH═CH—;
Z is —NH—, —CH$_2$—, —O— or ═CH—;
A$^1$ is a group

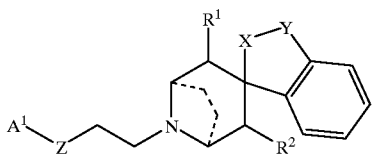

B is —(CH$_2$)$_m$—;
m is 0, 1 or 2;
R$^1$ and R$^2$ are each independently hydrogen or lower alkyl;

R$^3$ is hydrogen or halogen;
R$^4$ is hydrogen or hydroxy and
the dotted line is (—CH$_2$—CH$_2$—)$_n$, and n' is 0 or 1, or a pharmaceutically acceptable acid addition salt thereof.

Preferably, the compound of formula 1-1 is a compound of the formula

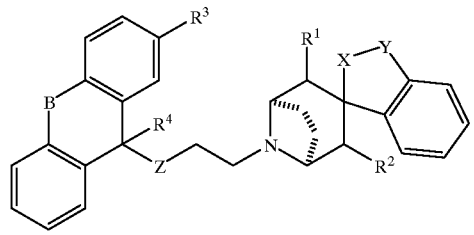

I-1a wherein

X is —O— or —CH$_2$—;
Y is —C(O)—, —(CH$_2$)$_n$ or —N(CH$_3$)—;
n is 1 or 2 or
X and Y taken together are —CH═CH—;
Z is —NH—, —CH$_2$—, —O— or ═CH—;
B is —(CH$_2$)$_m$;
m is 0, 1 or 2;
R$^1$ and R$^2$ are each independently hydrogen or lower alkyl;
R$^3$ is hydrogen or halogen;
R$^4$ is hydrogen or hydroxy and
the dotted line is (—CH$_2$—CH$_2$—)$_n$, and n' is 0 or 1; or a pharmaceutically acceptable acid addition salt thereof.

Preferably, the compound of formula 1-1a is a compound of the formula

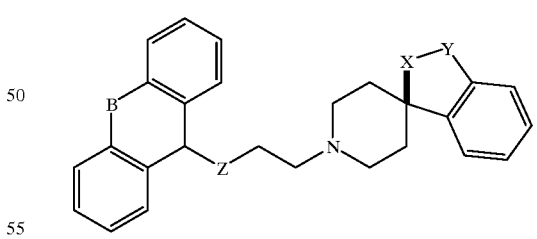

I-1a' wherein

X is O or —CH$_2$—;
Y is —C(O) or —CH$_2$;
Z is NH or —CH$_2$—;
B is —(CH$_2$)$_m$
m is 0 or 2, or a pharmaceutically acceptable acid addition salt thereof.

The compound of formula 1-1 may also be a compound of the formula

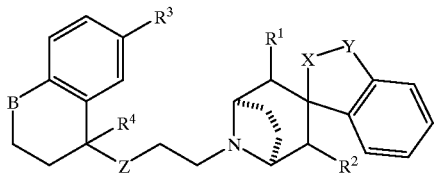

I-1b wherein
X is —O— or —CH$_2$—;
Y is —C(O)—, —(CH$_2$)$_n$— or —N(CH$_3$)—;
n is 1 or 2 or
X and Y taken together are —CH=CH—;
Z is —NH—, —CH$_2$—, —O— or =CH—;
B is —(CH$_2$)$_m$;
m is 0, 1 or 2;
R$^1$ and R$^2$ are each independently hydrogen or lower alkyl;
R$^3$ is hydrogen or halogen;
R$^4$ is hydrogen or hydroxy and
the dotted line is (—CH$_2$—CH$_2$—)$_{n'}$, and n' is 0 or 1; or a pharmaceutically acceptable addition salt thereof.

In another aspect, the invention relates to a method of treating a disease or disorder associated with overactivation of the OFQ receptor, comprising administering to a host in need of such treatment an effective amount of a compound of the formula

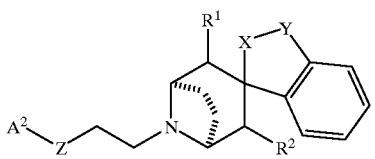

I-2 wherein
X is —O— or —CH$_2$—;
Y is —C(O)—, —(CH$_2$)$_n$— or —N(CH$_3$)—;
n is 1 or 2; or
X and Y taken together are —CH=CH—;
Z is —NH—, CH$_2$—, O or =CH—;
A$^2$ is diphenylmethyl;
R$^1$ and R$^2$ are hydrogen or lower alkyl; and
the dotted line is (—CH$_2$—CH$_2$—)$_{n'}$, and n' is 0 or 1, or a pharmaceutically acceptable acid addition salt thereof.

The compounds of formulas 1-1 and 1-2 are useful for the treatment of acute and/or chronic pain conditions. The compounds of formulas 1-1 and 1-2 are also useful for the treatment of metabolic disorders such as obesity. The compounds of formulas 1-1 and 1-2 are also useful for the treatment of memory and attention deficits, psychiatric, neurological and physiological disorders, especially, but not limited to, amelioration of symptoms of anxiety and stress disorders, depression, memory loss due to Alzheimer's disease or other dementias, epilepsy and convulsions, symptoms of addictive drug withdrawal, control of water balance, and Na$^+$ excretion and arterial blood pressure disorders.

DETAILED DESCRIPTION OF THE INVENTION

The invention relates to compounds of the formula

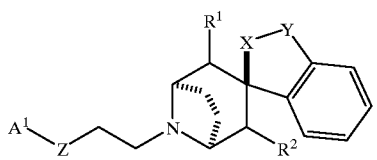

I-1 wherein
X is —O— or —CH$_2$—;
Y is —C(O)—, —(CH$_2$)$_n$— or —N(CH$_3$)—;
n is 1 or 2 or
X and Y taken together are —CH=CH—
Z is —NH—, —CH$_2$—, —O— or =CH—;
A$^1$ is a group a) b)

B is —(CH$_2$)$_m$—;
m is 0, 1 or 2;
R$^1$ and R$^2$ are each independently hydrogen or lower alkyl;
R$^3$ is hydrogen or halogen;
R$^4$ is hydrogen or hydroxy and
the dotted line is (—CH$_2$—CH$_2$—)$_{n'}$, and n' is 0 or 1, and to pharmaceutically acceptable acid addition salts thereof.

The compounds of formula I-1 and their salts are distinguished by valuable therapeutic properties. It has surprisingly been found that the compounds of the present invention are antagonists of the OFQ receptor. Consequently they will be useful in the treatment of acute and/or chronic pain conditions. The compounds of formulas 1-1 are also useful for the treatment of metabolic disorders such as obesity. The compounds of formulas 1-1 are also useful for the treatment of memory and attention deficits, psychiatric, neurological and physiological disorders, especially, but not limited to, amelioration of symptoms of anxiety and stress disorders, depression, memory loss due to Alzheimer's disease or other dementias, epilepsy and convulsions, symptoms of addictive drug withdrawal, control of water balance, and Na$^+$ excretion and arterial blood pressure disorders.

Objects of the present invention are the compounds of formula I-1 per se and pharmaceutically acceptable addition salts thereof, racemic mixtures and their corresponding enantiomers, the preparation of the above-mentioned compounds, medicaments containing them and their manufacture as well as the use of the above-mentioned compounds in the control or prevention of illnesses, especially of illnesses and disorders of the kind referred to earlier.

A further object of the present invention is the use of compounds of formula

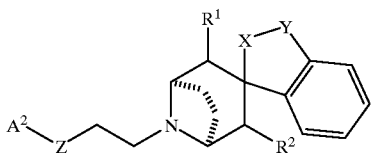

I-2 wherein A² is diphenylmethyl and all other substituents are as defined above and of their pharmaceutically usable salts for the treatment or prevention of memory and attention deficits, psychiatric, neurological and physiological disorders, especially, but not limited to, amelioration of symptoms of anxiety and stress disorders, memory loss due to Alzheimer's disease or other dementias, epilepsy and convulsions, symptoms of addictive drug withdrawal, control of water balance, Na⁺ excretion, arterial blood pressure disorders and metabolic disorders such as obesity or for the manufacture of corresponding medicaments.

Preferably, for compounds of formula I-2, n' is 0, X is O, Z is O or —NH—, and Y is —(CH₂)ₙ— or —C(O)—.

Most preferably, the compound of formula I-2 is 1'-(2-benzhydrdyloxy-ethyl)spiro[isobenzofuran-1(3H),4'-piperidine], 1'-(2-benzhydrdyloxy-ethyl)spiro[isobenzofuran-1,4'-piperidine]-3-one, or benzhydryl-(2-spiro[isobenzofuran-1(3H),4'-piperidin]-1'-yl-ethyl)-amine.

Compounds of formula I-2, in which X is O and A² is the group diphenylmethyl, are generically described in U.S. Pat. No. 3,985,889, incorporated herein by reference, and DE 24 58 176, as is their use as tranquilizer, antidepressive and analgetic agents.

The following definitions of the general terms used in the present description apply irrespective of whether the terms in question appear alone or in combination.

As used herein, the term "lower alkyl" denotes a straight- or branched-chain alkyl group containing from 1 to 6 carbon atoms, for example, methyl, ethyl, propyl, isopropyl, n-butyl, i-butyl, 2-butyl, t-butyl.

The term "halogen" denotes chlorine, iodine, fluorine and bromine.

"Leaving group" means a labile group that is replaced in a chemical reaction by another group. Examples of leaving groups are chlorine, bromine, iodine, trifluoromethylsulfonate, methanesulfonate or tosylate.

The present invention also relates compounds of the formula:

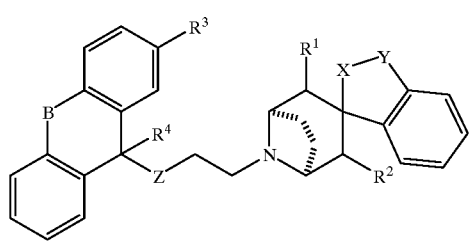

I-1a wherein
X is —O— or —CH₂—;
Y is —C(O)—, —(CH₂)ₙ or —N(CH₃)—;
n is 1 or 2 or
X and Y taken together may be —CH=CH—;

Z is —NH—, —CH₂—, —O— or =CH—;
B is —(CH₂)ₘ;
m is 0, 1 or 2;
R¹ and R² are each independently hydrogen or lower alkyl;
R³ is hydrogen or halogen;
R⁴ is hydrogen or hydroxy and
the dotted line is (—CH₂—CH₂—)ₙ, and n' is 0 or 1; and
to their pharmaceutically acceptable acid addition salts.

The present invention also relates to compounds of the formula:

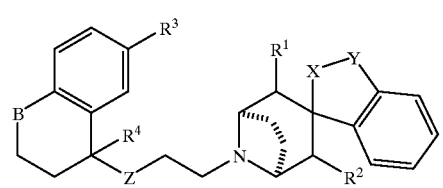

I-1b wherein
X is —O— or —CH₂—;
Y is —C(O)—, —(CH₂)ₙ or —N(CH₃)—;
n is 1 or 2 or
X and Y taken together may be —CH=CH—;
Z is —NH—, —CH₂—, —O— or =CH—;
B is —(CH₂)ₘ;
m is 0, 1 or 2;
R¹ and R² are each independently hydrogen or lower alkyl;
R³ is hydrogen or halogen;
R⁴ is hydrogen or hydroxy and
the dotted line is (—CH₂—CH₂—)ₙ, and n' is 0 or 1; and
to their pharmaceutically acceptable addition salts.

Exemplary preferred are compounds of the formula

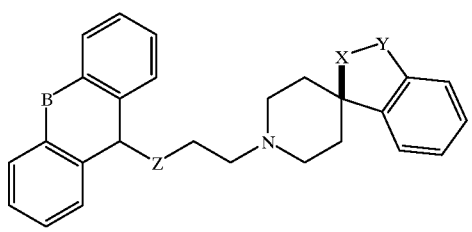

I-1a' wherein
X is O or —CH₂—;
Y is —C(O) or —CH₂;
Z is NH or —CH₂—;
B is —(CH₂)ₘ
m is 0 or 2
for example the following compounds:

1'-[2-(10,11-Dihydro-5H-dibenzo[a,d]cyclohepten-5-ylamino)-ethyl]-spiro[isobenzofuran-1,4'-piperidin]-3-one,
(10,11-dihydro-5H-dibenzo[a,d]cyclohepten-5-yl)-[2-(3H-spiro[isobenzofuran-1,4'-piperidin]-1'-yl)-ethyl]-amine,
(9H-fluoren-9-yl)-[2-(3H-spiro[isobenzofuran-1,4'-piperidin]-1'-yl)-ethyl]amine, 1'-[3-(10,11-dihydro-5H-dibenzo [a,d]cyclohepten-5-yl)-
propyl]-3H-spiro[isobenzofuran-1,4'-piperidine], 1'-[3-(10,11-dihydro-5H-dibenzo[a,d]cyclohepten-5-yl)-
propyl]-2,3-dihydro-spiro[indene-1,4'-piperidine].

The compounds of formula I-1 and their pharmaceutically acceptable salts can be prepared by methods known in the art, for example by processes described below, which comprise a) alkylating a compound of formula

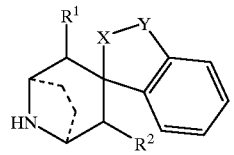

II with an alkylating agent of formula

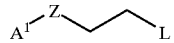

III to give a compound of formula I-1, wherein X, Y, $R^1$, $R^2$, Z and $A^1$ are as described as above and L is a leaving group, or b) reductively aminating a compound of formula II with an aldehyde of formula

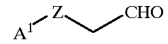

IV wherein $A^1$ and Z are as defined above, or c) reducing a compound of formula I-1, wherein Y is —C(O)— to a compound of formula I-1, wherein Y is —CH$_2$— and, d) if desired, converting the compound of formula I-1 obtained into a pharmaceutically acceptable acid addition salt.

The alkylation in accordance with process step a) is carried out in the presence of a base, such as triethylamine, morpholine, lithium carbonate, sodium carbonate or potassium carbonate in an inert solvent, for example acetonitrile, isobutylmethylketone, dimethylformamide or dimethylsulfoxide.

The alkylating reagent can be prepared by known methods, for example from the corresponding alcohol,

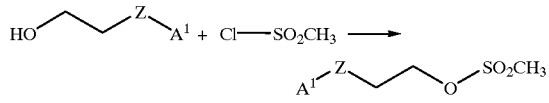

or from the corresponding amines with an a-halogenated acetic acid derivative such as chloroacetyl chloride or chloroacetyl bromide, followed by reduction of the formed amide to give the corresponding 2-halogen-ethylamine. As reducing agent borane or complexes thereof can be applied.

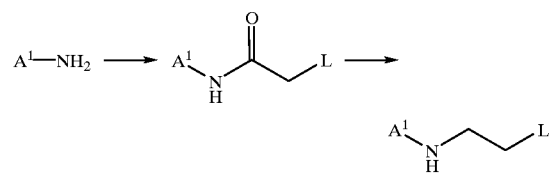

The reductive amination in accordance with process variant b) is carried out in conventional manner in a solvent, such as tetrahydrofurane, 1,2-dichloroethane, methanol or ethanol, and in the presence of a reducing agent, such as sodium cyanoborohydride or sodium triacetoxyborohydride.

Another method is the formation of an enamine from the reaction of II with IV with loss of water as the first step followed by reduction of this enamine to yield a compound of formula I-1 as the second step. Possible reducing agents in this case are borohydride, sodium cyanoborohydride and hydrogen in the presence of at least one hydrogenating catalyst, such as palladium on carbon, platinum or ruthenium.

Furthermore, compounds bearing the 3H-spiro[isobenzofuran-1,4'-piperidine] moity can be prepared from the corresponding spiro[isobenzofuran-1,4'-piperidine]-3-ones by reduction. Suitable reducing agents are for example borane, lithium-aluminium hydride, mixtures of boron trifluoride and complex hydrides such as sodium borohydride or lithium-aluminium hydride, sodium borohydride in acidic solution, lithium, phenyl silane or trichlorosilane and hydrogen in the presence of at least one catalyst such as platinum dioxide or Raney nickel.

If desired, compounds of formula I can be converted into a pharmaceutically acceptable acid addition salt. The salt formation is effected at room temperature with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methanesulphonates, p-toluenesulphonates and the like are examples of such salts.

The amines of formula II which are used as starting materials are known compounds or were prepared according to J. Org. Chem. 41 (1976), 2628 by lithiation of 2-bromobenzoic acid and reaction with the corresponding 1-benzyl-piperid-4-ones and subsequent debenzylation as follows:

Scheme 1

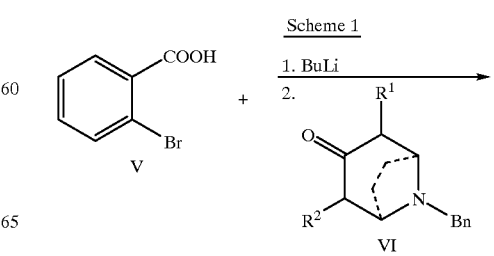

-continued

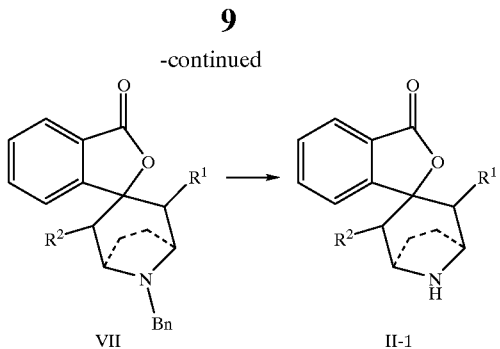

VII  II-1

The compounds of formulas III, IV, V and VI are known or can be prepared by known methods.

Compounds of formula I-2 can be prepared by methods known in the art, for example by processes described in U.S. Pat. No. 3,985,889, incorporated herein by reference, or by analagous methods.

As mentioned earlier, the compounds of formula I and their pharmaceutically usuable addition salts possess valuable pharmacodynamic properties. It has been found that the compounds of the present invention are antagonists of he OFQ receptor and have effects in animal models of memory and attention deficits, psychiatric, neurological and physiological disorders, such as anxiety, stress disorders, depression, memory loss due to Alzheimer's disease or other dementias, epilepsy and convulsions, acute and/or chronic pain conditions, symptoms of addictive drug withdrawal, control of water balance, $Na^+$ excretion, arterial blood pressure disorders and metabolic disorders such as obesity.

The compounds were investigated in accordance with the tests given hereinafter:

Methods of OFQ-R Binding Assay

Cell Culture

HEK-293 cells adapted to suspension growth (293s) were cultured in HL medium plus 2% FBS. The cells were transfected with the rat OFQ receptor cDNA (LC132), FEBS Lett. 347, 284–288, 1994, cloned in the expression vector pCEP4 (Invitrogen, San Diego, Calif., USA) using lipofectin (Life Technologies, Bethesda, Md., USA). Transfected cells were selected in the presence of hygromycin (1000 U/ml) (Calbiochem, San Diego, Calif., USA). A pool of resistant cells was tested for OFQ-R expression by binding of [$^3$H]-OFQ (Amersham PLC, Buckinghamshire, England). These cells (293s-OFQ-R) were expanded for large scale culture and membrane preparation.

Membrane Preparation

293s-OFQ-R cells were harvested by centrifugation, washed 3 times with phosphate buffered saline (PBS) before resuspension in buffer A (50 mM Tris-HCl, pH 7.8, 5 mM $MgCl_2$, 1 mM EGTA) and disruption with a tissue homogenizer (30 seconds, setting 4, Pt 20, Kinematica, Kriens-Lucern, Switzerland). A total membrane fraction was obtained by centrifugation at 49,000×g at 4° C. This procedure was repeated twice and the pellet was resuspended in buffer A. Aliquots were stored at −70° C. and protein concentrations were determined using the BCA™ Protein Assay Reagent (Pierce, Rockford, Ill.) following the manufacturer's recommendations.

Binding Assays

[$^3$H]-OFQ competition studies were carried out with 77 μg membrane protein in a final assay volume of 0.5 ml buffer A plus 0.1% BSA and 0.01% bacitracin (Boehringer-Mannheim, Mannheim, Germany) for one hour at room temperature. 50 nM unlabeled OFQ was used to define the non-specific binding. The assays were terminated by filtration through Whatman GF/C filters (Unifilter-96, Canberra Packard S.A., Zurich, Switzerland) pretreated with 0.3% polyethylenimine (Sigma, St. Louis, Mo., USA) and 0.1% BSA (Sigma) for 1 hour. The filters were washed 6 times with 1 ml of ice bold 50 mM Tris-HCl pH 7.5. The retained radioactivity was counted on a Packard Top-Count microplate scintillation counter after addition of 40 μl of Microscint 40 (Canberra Packard). The effects of compounds were determined using at least 6 concentrations in triplicate, and determined twice. $IC_{50}$ values were determined by curve fitting and these calues were converted to $K_i$ values by the method of Cheng and Prusoff, Biochem. Pharmacol., 22, 3099, 1973.

The affinity to the OFQ-receptor, given as pKi, is in the range of 6,7 to 8,2, for example the pKi for the compounds mentioned below is as follows:

| Example | Formula | OFQ pKi |
|---------|---------|---------|
| A/1 | | 7.3 |
| B/5 | | 7.0 |
| C | | 7.9 |

A/1 1'-[2-(10,11-Dihydro-5H-dibenzo[a,d]cyclohepten-5-ylamino)-ethyl]-spiro[isobenzofuran-1,4'-piperidin]-3-one methanesulfonate (1:2)
B/5 [2-(3H-Spiro[isobenzofuran-1,4'-piperidin]-1'-yl)-ethyl]-(5,6,7,8-tetrahydro-4H-benzocyclohepten-4-yl)-amine hydrochloride (1:2)
C 1'-(2-Benzhydryloxy-ethyl)-3H-spiro[isobenzofuran-1,4'-piperidine] hydrochloride (1:1)

The compounds of formula I-1 and 1-2 (collectively, compounds of formula I) as well as their pharmaceutically usuable acid addition salts can be used as medicaments, for example in the form of pharmaceutical preparations. The pharmaceutical preparations can be administered orally, for example in the form of tablets, coated tablets, dragées, hard and soft gelatine capsules, solutions, emulsions or suspensions. The administration can, however, also be effected rectally, for example in the form of suppositories, or parenterally, for example in the form of injection solutions.

The compounds of formula I and their pharmaceutically usuable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts and the like can be used as such excipients for example for tablets, dragées and hard gelatine capsules.

Suitable excipients for soft gelatine capsules are for example vegetable oils, waxes, fats, semi-solid and liquid polyols and the like.

Suitable excipients for the manufacture of solutions and syrups are for example water, polyols, saccharose, invert sugar, glucose and the like.

Suitable excipients for injection solutions are for example water, alcohols, polyols, glycerol, vegetable oils and the like.

Suitable excipients for suppositories are for example natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or anti-oxidants. They can also contain still other therapeutically valuable substances.

The dosage can vary within wide limits and will, of course, be fitted to the individual requirements in each particular case. In general, in the case of oral administration a daily dosage of about 10 to 1000 mg per person, preferably about 50–500 mg per person, of a compound of general formula I should be appropriate, although the above upper limit can also be exceeded when it appears to be indicated.

The following examples illustrate the present invention, but are not intended to be limiting in any manner.

EXAMPLE 1

1'-[2-(10,11-Dihydro-5H-dibenzo[a,d]cyclohepten-5-ylamino)-ethyl]-spiro[isobenzofuran-1,4'-piperidin]-3-one methansulfonate (1:2)

5-Amino-10,11-dihydro-5H-dibenzo[a,d]cycloheptene (10 mmol) was dissolved in acetone (25 ml) and sodium carbonate (1.6 g) was added. The mixture was cooled (0–5° C.) and chloroacetyl chloride (15 mmol) was added slowly. After stirring for 1 h at room temperature water (25 ml) and ethyl acetate (25 ml) were added. The organic phase was separated, washed with saturated NaHCO$_3$ solution, dried (MgSO$_4$) and concentrated to yield 88% of the chloroacetamide, which was used without further purification. Crude chloroacetamide (4 mmol) was dissolved in THF (10 ml). At 0–5° C. borane-THF-complex (1M solution in THF, 12 ml) was added slowly under argon. The mixture was stirred for 2 h at room temperature. After addition of hydrochloric acid (4M, 8 ml) the mixture was stirred for 15 min and then concentrated. The residue was partitioned between dichloromethane (10 ml) and saturated NaHCO$_3$ solution (10 ml) and the pH of the aqueous phase was adjusted to 8–9 with concentrated NaOH solution. The organic layer was separated, the aqueous layer was extracted several times with dichloromethane and the combined organic phases were dried (MgSO$_4$). Evaporation yielded the crude 2-chloroethyl-amine. This compound was dissolved in DMF (15 ml), then spiro[isobenzofuran-1(3H),4'-piperidin]-3-one (4 mmol), potassium carbonate (5.5 mmol) and potassium iodide (0.2 mmol) was added. After 3 h at 140° C. the solvent was evaporated under reduced pressure. Saturated NaHCO$_3$ solution was added and the mixture was extracted with dichloromethane. The combined organic layers were dried (MgSO$_4$) and concentrated. The residue was chromatographed over silicagel (ethylacetate). Addition of methanesulfonic acid to a solution of the product in ethylacetate/ethanol yielded 1'-[2-(10,11-Dihydro-5H-dibenzo[a,d]cyclohepten-5-ylamino)-ethyl]-spiro[isobenzofuran-1,4'-piperidin]-3-one methansulfonate (1.06 g, 42%) as colorless solid, m.p. 196° C.

EXAMPLE 2

1'-[2-(3-Chloro-10,11-dihydro-5H-dibenzo[a,d]cyclohepten-5-ylamino)-ethyl]-spiro[isobenzofuran-1,4'-piperidin]-3-one hydrochloride (1:2)

The title compound, m.p. 228° C. and MS: m/e=473 (M+H$^+$), was prepared in accordance with the general method of example 1 from 5-amino-3-chloro-10,11-dihydro-5H-dibenzo[a,d]cycloheptene, chloroacetyl chloride, spiro[isobenzofuran-1(3H),4'-piperidin]-3-one and Hcl.

EXAMPLE 3

(10,11-Dihydro-5H-dibenzo[a,d]cyclohepten-5-yl)-[2-(3H-spiro[isobenzofuran-1,4'-piperidin]-1'-yl)-ethyl]-amine hydrochloride (1:2)

The title compound, m.p. 215° C. and MS: m/e=425.3 (M+H$^+$), was prepared in accordance with the general method of example 1 from 5-amino-10,11-dihydro-5H-dibenzo[a,d]cycloheptene, chloroacetyl chloride, spiro[isobenzofuran-1(3H),4'piperidine] and Hcl.

EXAMPLE 4

(9H-Fluoren-9-yl)-[2-(3H-spiro[isobenzofuran-1,4'-piperidin]-1'-yl)-ethyl]-amine hydrochloride (1:2)

The title compound, m.p. 244° C. and MS: m/e=397.3 (M+H$^+$), was prepared in accordance with the general method of example 1 from 9-amino-fluorene, chloroacetyl chloride, spiro[isobenzofuran-1(3H),4'-piperidine] and Hcl.

EXAMPLE 5

[2-(3H-Spiro[isobenzofuran-1,4'-piperidin]-1'yl)-ethyl]-(5,6,7,8-tetrahydro-4H-benzocyclohepten-4-yl)-amine hydrochloride (1:2)

The title compound, m.p. 220° C. and MS: m/e=377.3 (M+H$^+$), was prepared in accordance with the general method of example 1 from (5,6,7,8-tetrahydro-4H-benzocyclohepten-4-yl)-amine, chloroacetyl chloride, spiro[isobenzofuran-1(3H),4'-piperidine] and Hcl.

EXAMPLE 6

(10,11-Dihydro-5H-dibenzo[a,d]cyclohepten-5-yl)-[2-(2,3-dihydro-spiro[indene-1,4'-piperidin]-1'-yl)-ethyl]-amine hydrochloride (1:2)

The title compound, m.p. 170° C. and MS: m/e=423.4 (M+H$^+$), was prepared in accordance with the general method of example 1 from 5-amino-10,11-dihydro-5H-dibenzo[a,d]cycloheptene, chloroacetyl chloride, 2,3-dihydro-spiro[1H-indene-1,4'-piperidine] and Hcl.

EXAMPLE 7

(10,11-Dihydro-5H-dibenzo[a,d]cyclohepten-5-yl)-[2-(spiro[indene-1,4'-piperidin]-1'-yl)-ethyl]-amine hydrochloride (1:2)

The title compound, m.p. 186° C. and MS: m/e=421.3 (M+H$^+$), was prepared in accordance with the general method of example 1 from 5-amino-10,11-dihydro-5H-dibenzo[a,d]cycloheptene, chloroacetyl chloride, spiro[1H-indene-1,4'-piperidine] and Hcl.

EXAMPLE 8

1'-[3-(10,11-Dihydro-5H-dibenzo[a,d]cyclohepten-5-yl)-propyl]-spiro[isobenzofuran-1,4'-piperidin]-3-one hydrochloride (1:1)

A solution of 3-(10,11-dihydro-5H-dibenzo[a,d]cyclohepten-5-yl)-propan-3-ol (1 mmol) and triethylamine (1.5 mmol) in dichloromethane was cooled to 0–5° C. A solution of methanesulfonyl chloride (1.5 mmol) in dichloromethane (1.5 ml) was added dropwise. After stirring for 1 h at 0–5° C., the mixture was concentrated under reduced pressure to yield the crude methanesulfonate as an oil. This was dissolved in acetonitrile together with spiro [isobenzofuran-1(3H),4'-piperidin]-3-one (1 mmol) and potassium carbonate (2.5 mmol) followed by reflux for 20 h. After evaporating the solvent saturated NaHCO$_3$ solution was added and the mixture was extracted with dichloromethane. The combined organic layers were dried (MgSO$_4$) and concentrated. The residue was chromatographed over silicagel (ethylacetate). Addition of HCl in ethanol to a solution of the product in ethylacetate/ethanol yielded 1'-[3-(10,11-dihydro-5H-dibenzo[a,d]cyclohepten-5-yl)-propyl]-spiro[isobenzofuran-1,4'-piperidin]-3-one hydrochloride (0.25 g, 53%) as colorless solid, m.p. 210° C. and MS: m/e=438.4 (M+H$^+$).

EXAMPLE 9

1'-[3-(5-Hydroxy-10,11-dihydro-5H-dibenzo[a,d] cyclohepten-5-yl)-propyl]-spiro[isobenzofuran-1,4'-piperidin]-3-one hydrochloride (1:1)

The title compound, m.p. 178° C. and MS: m/e=454.5 (M+H$^+$), was prepared in accordance with the general method of example 8 from 3-(5-hydroxy-10,11-dihydro-5H-dibenzo[a,d]cyclohepten-5-yl)-propan-3-ol and spiro [isobenzofuran-1(3H),4'-piperidin]-3-one.

EXAMPLE 10

1'-[3-(10,11-Dihydro-5H-dibenzo[a,d]cyclohepten-5-yl)-propyl]-3H-spiro[isobenzofuran-1,4'-piperidine] hydrochloride (1:1)

The title compound, m.p. 235° C. and MS: m/e=424.3 (M+H$^+$), was prepared in accordance with the general method of example 8 from 3-(10,11-dihydro-5H-dibenzo[a,d]cyclohepten-5-yl)-propan-3-ol and spiro[isobenzofuran-1 (3H),4'-piperidine].

EXAMPLE 11

5-[3-(3H-Spiro[isobenzofuran-1,4'-piperidin]-1'-yl)-propyl]-10,11-dihydro-5H-dibenzo[a,d]cyclohepten-5-ol hydrochloride (1:1)

The title compound, m.p. 201° C. and MS: m/e=440.3 (M+H$^+$), was prepared in accordance with the general method of example 8 from 5-[3-hydroxypropyl]-10,11-dihydro-5H-dibenzo[a,d]cyclohepten-5-ol and spiro [isobenzofuran-1(3H),4'-piperidine].

EXAMPLE 12

1'-[3-(10,11-Dihydro-5H-dibenzo[a,d]cyclohepten-5-ylidene)-propyl]-3H-spiro[isobenzofuran-1,4'-piperidine] hydrochloride (1:1)

The title compound, m.p. 231° C. and MS: m/e=422.3 (M+H$^+$), was prepared in accordance with the general method of example 8 from 3-(10,11-dihydro-5H-dibenzo[a,d]cyclohepten-5-ylidene)-propan-3-ol and spiro [isobenzofuran-1(3H),4'-piperidine].

EXAMPLE 13

1'-[3-(10,11-Dihydro-5H-dibenzo[a,d]cyclohepten-5-yl)-propyl]-2,3-dihydro-spiro[indene-1,4'-piperidine] hydrochloride (1:1)

The title compound, m.p. 220° C. and MS: m/e=422.3 (M+H$^+$), was prepared in accordance with the general method of example 8 from 3-(10,11-dihydro-5H-dibenzo[a, d]cyclohepten-5-yl)-propan-3-ol and 2,3-dihydro-spiro [indene-1,4'-piperidine].

EXAMPLE 14

1'-[3-(10,11-Dihydro-5H-dibenzo[a,d]cyclohepten-5-yl)-propyl]-spiro[indene-1,4'-piperidine] hydrochloride (1:1)

The title compound, m.p. 227° C. and MS: m/e=420.3 (M+H$^+$), was prepared in accordance with the general method of example 8 from 3-(10,11-dihydro-5H-dibenzo[a, d]cyclohepten-5-yl)-propan-3-ol and spiro[indene-1,4'-piperidine].

EXAMPLE 15

(1RS,3'SR)-1'-[3-(10,11-Dihydro-5H-dibenzo[a,d] cyclohepten-5-yl)-propyl]-3'-methyl-spiro [isobenzofuran-1,4'-piperidin]-3-one hydrochloride (1:1)

The title compound, m.p. 214° C. and MS: m/e=452.4 (M+H$^+$), was prepared in accordance with the general method of example 8 from 3-(10,11-dihydro-5H-dibenzo[a, d]cyclohepten-5-yl)-propan-3-ol and (1RS,3'SR)-3'-methyl-spiro[isobenzofuran-1,4'-piperidin]-3-one.

EXAMPLE 16

(1RS,3'SR)-1'-[3-(10,11-Dihydro-5H-dibenzo[a,d] cyclohepten-5-yl)-propyl]-3'-methyl-spiro [isobenzofuran-1,4'-piperidine] hydrochloride (1:1)

(1RS,3'SR)-1'-[3-(10,11-Dihydro-5H-dibenzo[a,d] cyclohepten-5-yl)-propyl]3'-methyl-spiro[isobenzofuran-1, 4'-piperidin]-3-one (0.5 mmol) was dissolved in tetrahydrofurane and borane-THF-complex (1M solution in THF, 3 mmol) was added under argon. The resulting mixture was heated at reflux for 18 h. It was cooled to 0° C., and 1M HCl was added dropwise until no more gas evolution was observed. The mixture was concentrated in vacuo and HCl (1N, 5 ml) was added to the white foam obtained, and the resulting mixture was stired at 100° C. for 1 h. The solution was then cooled and basified with concentrated aqueous ammonia solution. The product was extracted into dichloromethane and purified by column chromatography over silicagel (ethylacetate). Addition of HCl in ethanol to a solution of the product in ethylacetate/ethanol yielded (1RS, 3'SR)-1'-[3-(10,11-dihydro-5H-dibenzo[a,d]cyclohepten-5-yl)-propyl]-3'-methyl-spiro[isobenzofuran-1,4'-piperidine] hydrochloride (0.18 g, 82%) as colorless solid, m.p. 225° C. and MS: m/e=438.4 (M+H$^+$).

EXAMPLE 17

(1R,3'R,5'S)-1'-[3-(10,11-Dihydro-5H-dibenzo[a,d] cyclohepten-5-yl)-propyl]-3',5'-dimethyl-3H-spiro [isobenzofuran-1,4'-piperidine] hydrochloride (1:1)

The title compound, m.p. 237° C. and MS: m/e=452.5 (M+H$^+$), was prepared in accordance with the general method of example 8 from 3-(10,11-dihydro-5H-dibenzo[a, d]cyclohepten-5-yl)-propan-3-ol and (1R,3'R,5'S)-3',5'-dimethyl-3H-spiro[isobenzofuran-1,4'-piperidine] followed by borane reduction according to example 16.

EXAMPLE 18

1'-[3-(10,11-Dihydro-5H-dibenzo[a,d]cyclohepten-5-yl)-propyl]-1-methyl-1,2-dihydro-spiro[indole-3,4'-piperidine] hydrochloride (1:1)

For the synthesis of the title compound, m.p. 222° C. and MS: m/e=437.4 (M+H$^+$), 1-methyl-spiro[3H-indole-3,4'- piperidin]-2(1H)-one is reduced with borane according to example 16 to yield 1-methyl-1,2-dihydro-spiro[indole-3,4'-piperidine], which was further reacted with 3-(10,11-dihydro-5H-dibenzo[a,d]cyclohepten-5-yl)-propan-3-ol in accordance with the general method of example 8.

EXAMPLE 19

(10,11-Dihydro-5H-dibenzo[a,d]cyclohepten-5-yl)-[2-(spiro[isochroman-1,4'-piperidin]-1'-yl)-ethyl]-amine hydrochloride (1:2)

The title compound, m.p. 190° C. and MS: m/e=439.4 (M+H$^+$), was prepared in accordance with the general method of example 1 from 5-amino-10,11-dihydro-5H-dibenzo[a,d]cycloheptene, chloroacetyl chloride, spiro[isochroman-1,4'-piperidine] and Hcl.

EXAMPLE 20

1'-[3-(9,10-Dihydro-5H-dibenzo[a,d]cyclohepten-5-yl)-propyl]-spiro[isochroman-1,4'-piperidine] hydrochloride (1:1)

The title compound, m.p. 243° C. and MS: m/e=438.4 (M+H$^+$), was prepared in accordance with the general method of example 8 from 3-(10,11-dihydro-5H-dibenzo[a,d]cyclohepten-5-yl)-propan-3-ol and spiro[isochroman-1,4'-piperidine].

EXAMPLE 21

(1RS,5SR)-8-[3-(9,10-Dihydro-5H-dibenzo[a,d]cyclohepten-5-yl)-propyl]-spiro[8-aza-bicyclo[3.2.1]octane-3,1'-isobenzofuran]-3'-one hydrochloride (1:1)

The title compound, m.p. 284° C. and MS: m/e=464.3 (M+H$^+$), was prepared in accordance with the general method of example 8 from 3-(10,11-dihydro-5H-dibenzo[a,d]cyclohepten-5-yl)-propan-3-ol and (1RS,5SR)-spiro[8-aza-bicyclo[3.2.1]octane-3,1'-isobenzofuran]-3'-one__1RS,3'SR)-3'-methyl-spiro[isobenzofuran-1,4'-piperidin]-3-one.

Synthesis of Intermediates

EXAMPLE 22

(1RS,3'SR)-3'-Methyl-spiro[isobenzofuran-1,4'-piperidin]-3-one

2-Bromobenzoic acid (70 mmol) was added to a dry three-necked flask equipped with an addition funnel, low temperature thermometer, inert gas inlet, and mechanical stirrer. Dry tetrahydrofurane (250 ml) was added and the solution was cooled to –78° C. n-Butyl-lithium was added slowly (2 h) while maintaining the mixture below –70° C. and the resulting solution was stirred for an additional 1 h. 1-Benzyl-3-methyl-piperid-4-one (98 mmol) in a mixture of hexane and tetrahydrofurane (25 ml/25 ml) was added over 30 min while maintaining the mixture below –70° C. (within 1 h) and the mixture was allowed to warm to room temperature. After stirring overnight the mixture was poured into water (300 ml), extracted with ether and was acidified with concentrated HCl (to pH 2–3) and extracted with ether. The acidic solution was boiled for 1 h and was then cooled (0–5° C.) and made alkaline (to pH 9–10) with aqueous NaOH. The cold solution was extracted with dichloromethane. The combined organic extracts were dried (MgSO$_4$) and concentrated to give a yellow oil (7.0 g). This was chromatographed over silicagel (ethylacetate) to yield 6.35 g of (1RS,3'SR)-1'-benzyl-3'-methyl-spiro[isobenzofuran-1,4'-piperidin]-3-one a colorless oil (20.6 mmol, 30%). For debenzylation this compound was dissolved in ethanol (250 ml) and palladium on charcoal (10%, 0.64 g) was added. The suspension was stirred and hydrogenated (1 bar) overnight. After filtering off the catalyst the solution was concentrated. The remaining solid was recrystallized from ethyl acetate to yield (1RS,3'SR)-3'-methyl-spiro[isobenzofuran-1,4'-piperidin]-3-one as colorless solid (2.7 g, 60%), m.p. 131° C. and MS: m/e=218.3 (M+H$^+$).

EXAMPLE 23

(1R,3'R,5'S)-3',5'-Dimethyl-3H-spiro[isobenzofuran-1,4'-piperidin]-3-one

The title compound, m.p. 125° C. and MS: m/e=231 (M$^+$), was prepared in accordance with the method for the synthesis of (1RS,3'SR)-3'-methyl-spiro[isobenzofuran-1,4'-piperidin]-3-one using 1-benzyl-3,5-dimethyl-piperid-4-one.

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely

What is claimed is:

1. A compound of the formula

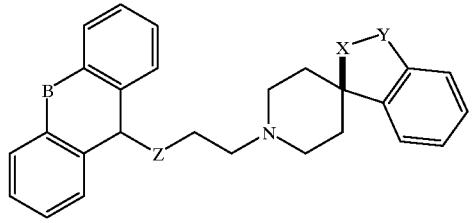

I-1a' wherein
X is O or —CH$_2$—;
Y is —C(O) or —CH$_2$;
Z is NH or —CH$_2$—;
B is —(CH$_2$)$_m$
m is 0 or 2, or a pharmaceutically acceptable acid addition salt thereof.

2. A compound in accordance with claim 1, wherein X is O.

3. A compound in accordance with claim 1, wherein X is —CH$_2$—.

4. A compound in accordance with claim 1, wherein Y is —C(O).

5. A compound in accordance with claim 1, wherein Y is —CH$_2$.

6. A compound in accordance with claim 1, wherein Z is NH.

7. A compound in accordance with claim 1, wherein Z is —CH$_2$—.

8. A compound in accordance with claim 1, wherein m is 0.

9. A compound in accordance with claim 1, wherein m is 2.

10. A compound in accordance with claim 1, 1'-[2-(10,11-Dihydro-5H-dibenzo[a,d]cyclohepten-5-ylamino)-ethyl]-spiro[isobenzofuran-1,4'-piperidin]-3-one.

11. A compound in accordance with claim 1, (10,11-dihydro-5H-dibenzo[a,d]cyclohepten-5-yl)-[2-(3H-spiro[isobenzofuran-1,4'-piperidin]-1'-yl)-ethyl]-amine.

12. A compound in accordance with claim 1, (9H-fluoren-9-yl)-[2-(3H-spiro[isobenzofuran-1,4'-piperidin]-1'-yl )-ethyl]-amine.

13. A compound in accordance with claim 1, 1'-[3-(10,11-dihydro-5H-dibenzo[a,d]cyclohepten-5-yl)-propyl]-3H-spiro-[isobenzofuran-1,4'-piperidine].

14. A compound in accordance with claim 1, 1'-[3-(10,11-dihydro-5H-dibenzo[a,d]cyclohepten-5-yl)-propyl]-2,3-dihydro-spiro[indene-1,4'-piperidine].

* * * * *